United States Patent [19]

Souma

[11] Patent Number: 4,990,629
[45] Date of Patent: Feb. 5, 1991

[54] PROCESS FOR PRODUCING LACTONES

[75] Inventor: Yoshie Souma, Ibaraki, Japan

[73] Assignee: Agency of Industrial Science & Technology, Tokyo, Japan

[21] Appl. No.: 292,856

[22] Filed: Jan. 3, 1989

[51] Int. Cl.$^5$ .................. C07D 321/00; C07D 319/12
[52] U.S. Cl. ................................. 549/267; 549/274
[58] Field of Search .......................... 549/267, 274

[56] References Cited

U.S. PATENT DOCUMENTS

| | | | |
|---|---|---|---|
| 3,910,963 | 10/1975 | Souma et al. | 549/266 |
| 4,052,988 | 10/1977 | Doddi | 128/335.5 |
| 4,070,375 | 1/1978 | Suzuki | 260/340.6 |
| 4,142,057 | 2/1979 | Suzuki | 562/525 |

OTHER PUBLICATIONS

Souma, "Carbonylation of Dienes and Diols in the Presence of Copper (I) Carbonyl Catalysts", CA 86 155170e (1977).

Primary Examiner—Glennon H. Hollrah
Assistant Examiner—Amelia A. Owens
Attorney, Agent, or Firm—Armstrong, Nikaido, Marmelstein, Kubovcik & Murray

[57] ABSTRACT

Lactones of the following general formula:

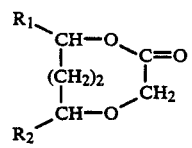

wherein $R_1$ and $R_2$ each represent a hydrogen atom or an alkyl group and n represents an integer of 0 to 10, are produced by reacting a diol, formaldehyde and carbon monoxide in the presence of copper (I) or silver carbonyl complex catalyst in a strong acid.

6 Claims, No Drawings

PROCESS FOR PRODUCING LACTONES

BACKGROUND OF THE INVENTION

The present invention relates to a process for producing lactones. In particular, the present invention relates to a process for producing lactones in a high yield by reacting a diol, formaldehyde and carbon monoxide in the presence of a catalyst under around atmospheric pressure.

1,4-Dioxan-2-one, 1,4-dioxepan-2-one and derivatives of them produced by reacting ethylene glycol or 1,3-propanediol with formaldehyde and carbon monoxide are hopeful as starting materials for absorbable sutures or wound healing compounds. However, these lactones are usually difficultly available on the market.

A production process according to the disclosure of U.S. Pat. No. 4,070,375 is not always easy, because carbon monoxide of a pressure as high as 140 atm must be subjected to the reaction in highly corrosive hydrogen fluoride. Further this process requires high costs of the equipment and operation, because a highly anticorrosive pressure vessel is necessitated as the production apparatus.

Under these circumstances, the development of a process wherein the pressure of carbon monoxide to be reacted is lowered or a process wherein a less expensive apparatus is used has been eagerly demanded.

BRIEF SUMMARY OF THE INVENTION

A first object of the present invention is to provide a process for producing lactones wherein the pressure of carbon monoxide used is lower than that used in conventional processes.

A second object of the present invention is to provide a process for producing lactones at low equipment and operation costs and, therefore, at low production costs.

A third object of the present invention is to provide a process for producing lactones a large demand of which is expected in the medical industry.

The above objects of the present invention can be attained by a process wherein a diol, formaldehyde and carbon monoxide are reacted together in the presence of a copper (I) or silver carbonyl complex catalyst in a strong acid to form a lactone of the following general formula:

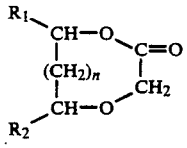

wherein $R_1$ and $R_2$ each represent a hydrogen atom or an alkyl group and n represents an integer of 0 to 10.

THE PREFERRED EMBODIMENTS

In the present invention, a copper (I) or silver carbonyl complex is used as the catalyst for the carbonylation with carbon monoxide. The carbonyl complex can be produced by introducing carbon monoxide into a compound capable of giving a cuprous ion or a silver compound in a strong acid as shown in the following formulae:

$$Cu^+ + (n+1)CO \rightarrow Cu(CO)_n^+ + Cu(CO)^+ \quad (1)$$

$$Ag^+ + 2CO \rightarrow Ag(CO)_2^+ \quad (2)$$

$Cu(CO)_n^+$ in the above formula (1) and $Ag(CO)_2^+$ in the above formula (2) are catalytically active elements called copper (I) carbonyl ion and silver carbonyl ion, respectively.

The compounds capable of giving a cuprous ion include, for example, cuprous oxide, cuprous sulfate and an equimolar mixture of a cupric compound such as cupric sulfate, cupric oxide or cupric acetate with copper powder.

The silver compounds usable herein include, for example, silver oxide, silver sulfate and silver borofluoride.

The strong acids usable herein include, for example, sulfuric acid, boron trifluoride/water complex, hydrogen fluoride and phosphoric acid having a concentration of at least 80%. They may be used either singly or as a combination of two or more of them.

The reaction temperature in the production of the complex catalyst varies depending on the kind of the strong acid used. It may be equal to the carbonylation reaction temperature which will be described below.

The amount of carbon monoxide absorbed in the production of the carbonyl complex is $1 < CO/Cu < 4$ for the copper compound and $0.1 < CO/Ag < 2$ for the silver compound. Thus a solution of the copper (I) or silver carbonyl complex in the strong acid is formed.

In the present invention, equimolar amounts of the diol and formaldehyde are added to the complex solution and then carbon monoxide is introduced thereinto under stirring to conduct the carbonylation reaction.

The diols include, for example, ethylene glycol, 1,3-propanediol, 1,2-propanediol, 1,3-butanediol, 1,4-butanediol, 2,3-butanediol, pentanediols, hexanediols, heptanediols, octanediols, nonanediols, decanediols and dodecanediols.

Formaldehyde is preferably anhydrous paraformaldehyde or trioxane.

The carbonylation reaction in which an equimolar amount of carbon monoxide is reacted to form a lactone is represented by the following formula:

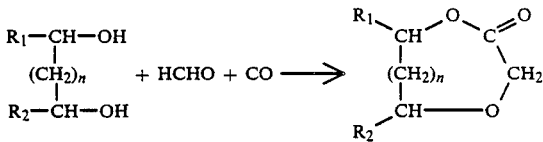

wherein $R_1$ and $R_2$ each represent a hydrogen atom or an alkyl group having 1 to 5 carbon atoms and n represents an integer of 0 to 10.

The reaction proceeds sufficiently under atmospheric pressure, i.e. under a carbon monoxide pressure of 1 atm. However, the pressure of carbon monoxide is preferably 0.5 to 10 atm, particularly 1 to 5 atm, since the reaction is accelerated under an elevated pressure. The term "0.5 atm carbon monoxide" indicates a gaseous mixture having a CO partial pressure of 0.5 atm prepared by diluting carbon monoxide to 50% with $N_2$, $H_2$, $CO_2$ or the like or a waste gas from a blast furnace. The reaction temperature is 0° to 50° C. when sulfuric acid or boron trifluoride/water complex is used as the solvent and $-10°$ to 15° C. when hydrogen fluoride is used.

After the completion of the reaction, the reaction mixture is poured into ice/water to separate the product from the catalyst layer. Thus the intended lactone is obtained.

By the process of the present invention for producing the lactones, an intended lactone can be produced under a carbon monoxide pressure of around atmospheric pressure, since a copper (I) or silver carbonyl complex is used as the catalyst, while a carbon monoxide pressure of 100 atm or above is necessitated in the conventional processes.

Therefore, the equipment and operation costs are remarkably reduced and the biocompatible materials having a high performance can be provided at low costs.

The following examples will further illustrate the present invention.

EXAMPLE 1

0.715 g of cuprous oxide and 20 ml of 98% sulfuric acid were placed in a three-necked glass flask connected to a carbon monoxide gas buret. Carbon monoxide was introduced thereinto under stirring to react the copper compound with carbon monoxide and to thereby form a copper carbonyl catalyst solution.

3.6 g (120 mmol) of paraformaldehyde and 6.0 ml (120 mmol) of ethylene glycol were slowly added to the catalyst solution at 30° C. under a carbon monoxide pressure of 1 atm and the mixture was stirred to conduct the reaction. Carbon monoxide was thus reacted with starting paraformaldehyde and ethylene glycol in equimolar amounts. After the completion of the reaction, the reaction mixture was poured into ice/water to separate the product from the catalyst layer. 10.4 g (85%) of 1,4-dioxan-2-one and 1.62 g (15%) of methyl glycolate were obtained.

EXAMPLE 2

0.928 g of a silver oxide and 20 ml of boron trifluoride/water complex were placed in a three-necked flask connected to a carbon monoxide buret. The mixture was stirred to form a silver carbonyl catalyst solution. 7.22 ml (100 mmol) of 1,3-propanediol and 3.0 g (100 mmol) of trioxane were slowly added to the catalyst solution at 25° C. under a carbon monoxide pressure of 1 atm and the mixture was stirred to conduct the reaction with carbon monoxide. The amount of carbon monoxide reacted was equimolar to the amounts of 1,3-propanediol and trioxane. After the completion of the reaction, the reaction mixture was poured into ice/water to separate the product from the catalyst layer. 7.0 g (yield: 60%) of 1,4-dioxepan-2-one was obtained.

EXAMPLE 3

0.572 g of cuprous oxide and 20 ml of hydrogen fluoride were placed in a Daiflon reaction vessel connected to a carbon monoxide buret, and reacted with carbon monoxide at 5° C. under 1 atm to form a copper carbonyl catalyst solution. 9.1 ml (100 mmol) of 1,3-butanediol and 3.0 g (100 mmol) of paraformaldehyde were slowly added to the catalyst solution at 5° C. and the mixture was stirred to conduct the reaction with carbon monoxide under 1 atm. 85 molar %, based on 1,3-butanediol, of carbon monoxide was reacted. The product was separated from the catalyst layer to obtain 9.1 g (yield: 70%) of 5-methyl-1,4-dioxepan-2-one.

EXAMPLE 4

0.86 g of cuprous oxide and 20 ml of 98% sulfuric acid were placed in a three-necked glass flask connected to a carbon monoxide buret. The mixture was stirred to react the copper compound with carbon monoxide to thereby form a copper carbonyl catalyst solution. 3.0 g (100 mmol) of paraformaldehyde and 7.3 ml (100 mmol) of 1,2-propanediol were slowly added to the catalyst solution under stirring at 30° C. under a carbon monoxide pressure of 1 atm to conduct the reaction with carbon monoxide. 95 molar %, based on starting 1,2-propanediol, of carbon monoxide was reacted. After the completion of the reaction, the reaction mixture was poured into ice/water to separate the product from the catalyst layer. 10.5 g (yield: 90%) of 5-methyl-1,4-dioxan-2-one was obtained.

EXAMPLE 5

Equimolar amounts of paraformaldehyde, dodecanediol and carbon monoxide were reacted in the same manner as that of Example 1 except that ethylene glycol was replaced with 24 g (120 mmol) of dodecanediol to obtain 5.8 g of a lactone having a mass number of 242. Yield: 20%.

What is claimed:

1. A process for producing a cyclo-1,4-dioxa-2-one of the formula

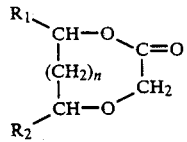

wherein $R_1$ and $R_2$ are each a hydrogen atom or an alkyl group and n is an integer of 0 to 10, which comprise reacting a diol of the formula

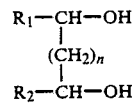

with formaldehyde and carbon monoxide in the presence of a strong acid and a copper (I) or silver carbonyl complex as the catalyst.

2. A process according to claim 1, wherein the strong acid is an acid selected from the group consisting of concentrated sulfuric acid, boron trifluoride/water complex and hydrogen fluoride.

3. A process according to claim 1, wherein the pressure of carbon monoxide is 0.5 to 10 atm.

4. A process according to claim 1, wherein the alkyl group has 1 to 5 carbon atoms.

5. A process according to claim 1, wherein the reaction temperature is −10° to 50° C.

6. A process according to claim 1, wherein the copper (I) or silver carbonyl complex is prepared by reacting Cu+ or Ag+ ions with carbon monoxide in the presence of a strong acid.

* * * * *